(12) United States Patent
Wolfenbarger

(10) Patent No.: US 10,335,582 B2
(45) Date of Patent: Jul. 2, 2019

(54) ALCOHOL PREP APPLICATOR

(71) Applicant: Guin Dale Wolfenbarger, Apple Valley, CA (US)

(72) Inventor: Guin Dale Wolfenbarger, Apple Valley, CA (US)

( * ) Notice: Subject to any disclaimer, the term of this patent is extended or adjusted under 35 U.S.C. 154(b) by 485 days.

(21) Appl. No.: 14/145,857

(22) Filed: Dec. 31, 2013

(65) Prior Publication Data

US 2015/0182738 A1    Jul. 2, 2015

(51) Int. Cl.
| | |
|---|---|
| *A61F 13/40* | (2006.01) |
| *A61F 13/15* | (2006.01) |
| *A61F 13/38* | (2006.01) |
| *A61M 35/00* | (2006.01) |
| *B05C 17/00* | (2006.01) |
| *B65D 47/42* | (2006.01) |
| *A61M 5/42* | (2006.01) |
| *A61M 5/32* | (2006.01) |
| *A61F 13/00* | (2006.01) |
| *A47L 25/00* | (2006.01) |
| *A47L 17/00* | (2006.01) |

(52) U.S. Cl.
CPC ........... *A61M 35/006* (2013.01); *A61F 13/00* (2013.01); *A61M 5/32* (2013.01); *A61M 5/42* (2013.01); *A47L 17/00* (2013.01); *A47L 25/00* (2013.01); *A61F 13/15* (2013.01); *A61F 13/38* (2013.01); *B05C 17/00* (2013.01); *B65D 47/42* (2013.01)

(58) Field of Classification Search
CPC .............................. A61M 35/006; A61F 13/40
See application file for complete search history.

(56) References Cited

U.S. PATENT DOCUMENTS

| | | | | | |
|---|---|---|---|---|---|
| 3,687,140 | A | * | 8/1972 | Reynolds | A61M 35/006 15/244.1 |
| 6,216,573 | B1 | * | 4/2001 | Moutafis | A61B 17/3203 417/413.1 |
| 6,551,265 | B1 | * | 4/2003 | Miguel | B43K 8/00 401/57 |
| 6,811,339 | B1 | * | 11/2004 | Tsaur | A45D 40/24 220/23.4 |
| 2005/0053413 | A1 | * | 3/2005 | Tsaur | A61M 35/006 401/133 |

(Continued)

*Primary Examiner* — Benjamin J Klein
*Assistant Examiner* — Sara A Sass
(74) *Attorney, Agent, or Firm* — Charles C. H. Wu; Charles C. H. Wu & Assoc., APC

(57) ABSTRACT

The present invention is an improved applicator comprising an applicator body having a top portion, a bottom portion and a central portion, a bladder positioned between the bottom portion and the central portion of the applicator body and designed for holding alcohol solution, a hinge lever extending from an inner side of the central portion and extending outwards from the top portion of the applicator body and a hinge door positioned on the central portion of the applicator body. The cartridge of swabs can be easily loaded by opening the hinge door and rests between the bottom portion and the central portion of the applicator body. The used swabs can be easily discarded by clicking the hinge lever. The improved applicator allows easy application of alcohol solution to the patient's skin in a simple and safe manner and provides a safe and convenient hand-held method for safe preparation of skin.

12 Claims, 6 Drawing Sheets

(56) References Cited

U.S. PATENT DOCUMENTS

2009/0324319 A1* 12/2009 Houde ............. A61B 17/00491
  401/138
2012/0003027 A1* 1/2012 Ballot .................. A46B 11/001
  401/108

* cited by examiner

ALCOHOL PREP APPLICATOR

BACKGROUND OF THE DISCLOSURE

Technical Field of the Disclosure

The present embodiment relates in general to a medical applicator for applying an anti-microbial solution to a patient's skin prior to a medical procedure. More specifically, the present embodiment relates to a device and method for applying an alcohol solution to a patient's skin that dispenses the alcohol solution from a swab when activated with a hinge lever.

Description of the Related Art

Standard invasive medical procedures require a patient's skin to be disinfected prior to the procedure. This skin preparation is important in order to reduce the risk of infection to the patient. Swabs are commonly used to disinfect the skin prior to surgical procedures. The use of such swabs carries inherent risks since the patient's skin is often exposed to bacteria which in turn are unhygienic. Hands free skin preparation techniques such as alcohol applicators are also used for applying surgical preparations. However, the conventional techniques utilizing applicators require additional preparation steps including an extended period of cleaning using anti-microbial solutions, followed by the application of an antiseptic or disinfectant which can be time-consuming.

An existing applicator for an anti-microbial solution includes a generally hollow handle having a closed proximal end and an open distal end; a foam pad attached to the hollow handle over the open distal end; and a slit formed in the foam pad that acts as a flow control valve. The hollow handle contains the anti-microbial solution. When the applicator is pressed against a patient's skin, the slit opens to allow the anti-microbial solution to flow past the slit into the foam pad and hence the anti-microbial solution can be easily distributed over the patient's skin by the foam pad. However, the anti-microbial solution is directly applied on the patient's skin using the foam pad which can cause irritation to patients having sensitive skin.

A variant to this applicator is another applicator having a substantially hollow body for accommodating an ampoule of solution. The applicator is designed for use with a glass ampoule having a breakable neck. The hollow body comprises an open proximal end for receiving the ampoule and an open distal end having a flange to accept an applicator pad for applying the solution. A back plug having a lever mechanism is inserted into the open proximal end of the applicator to activate the applicator and seal the applicator after activation. Advancement of the back plug lever mechanism into the hollow body pivots the body of the ampoule to break the neck, activating the applicator. The back plug seals the proximal end after activation of the applicator. While this applicator employs an efficient means for preparing skin prior to medical procedures, such applicator does not provide satisfactory means of ensuring safety to the user.

Yet another existing applicator for treating skin includes a housing in which a device for perforating an area of skin is arranged. The device can be brought into contact with the area of skin through an opening in the housing. The device for disinfecting is arranged in the housing, and the device acts upon the area of skin through the same opening. The downside to this applicator is that the applicator does not include any means to control the flow of anti microbial solution to the patient's skin.

Therefore it can be seen that there is a need for an improved disinfectant applicator that would provide for the safe preparation of skin. Such an applicator would be more hygienic and safe to the patient. This needed applicator would be able to adjust the flow of solution. The applicator would be easily placed in an applicator holder while not in use. The applicator would be simple and easy to handle, and provide a comfortable user and patient interface.

SUMMARY OF THE EMBODIMENT

The present invention is an improved applicator comprising an applicator body having a top portion, a bottom portion and a central portion, a bladder positioned between the bottom portion and the central portion of the applicator body and designed for holding alcohol solution, a plunger referred to herein as a hinge lever extending from an inner side of the central portion and extending outwards from the top portion of the applicator body and a hinge door positioned on the central portion of the applicator body. The improved applicator allows easy application of alcohol solution to the patient's skin in a simple and safe manner.

The present invention also discloses a method for preparing a patient's skin prior to medical procedures. Initially, the hinge door is opened and the hinge lever or plunger is pulled back. The applicator body is then loaded with the cartridge of swabs and the hinge door is closed. The bladder of the applicator body is flexible as it can be squeezed and placed in the alcohol solution so as to allow the bladder to expand by taking in the alcohol solution. Then, the patient's skin is swabbed utilizing a top portion of at least one swab extending from the bottom portion of the applicator body. The used swab is then discarded by clicking the hinge lever. The hinge lever or plunger is spring-loaded which is how the hinge lever achieves the pulling back motion for insertion of the cartridge of swabs, and the pressing or clicking which allows for discarding the used swab and advancing the next swab.

One objective of the present invention is to provide a safe and convenient hand-held method for preparation of skin prior to medical procedures.

A second objective of the present invention is to provide an improved applicator that can adjust the flow of alcohol solution.

A third objective of the present invention is to provide an improved applicator that can be placed in an application holder while not in use.

Another objective of the present invention is to provide an improved applicator that provides more hygiene and safety to the patient.

Yet another objective of the present invention is to provide an improved applicator that is easy to use.

These and other advantages and features of the present invention are described with specificity so as to make the present invention understandable to one of ordinary skill in the art.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

Figure 1:
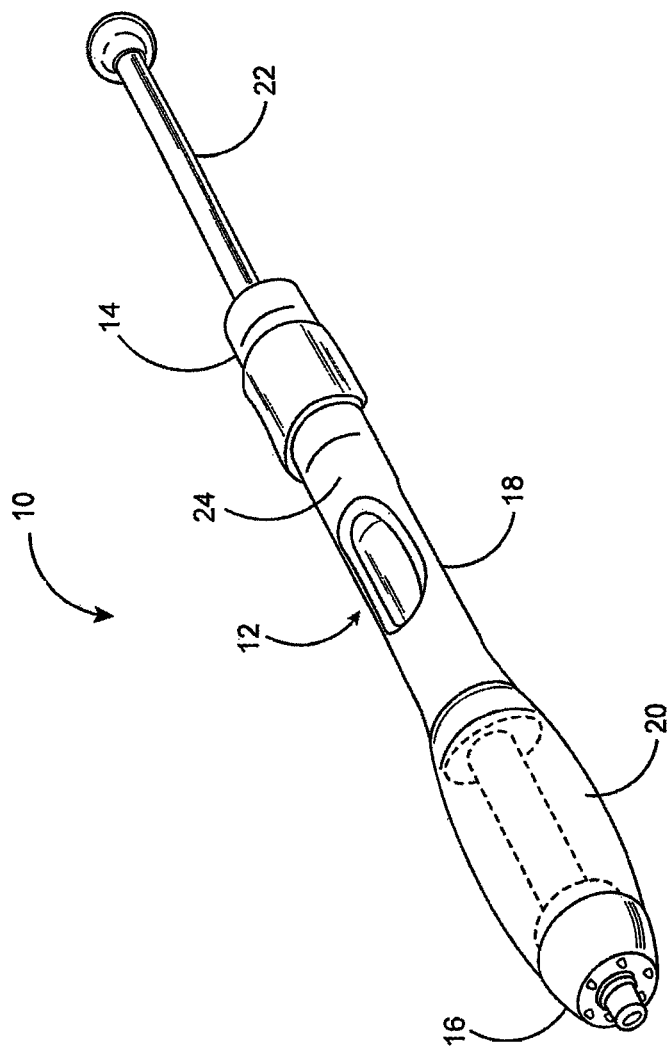
FIG. 1 illustrates a perspective view of an improved applicator of the present invention.

Referring to FIG. 1, a perspective view of an improved applicator 10 of the present invention is illustrated. The improved applicator 10 comprises an applicator body 12 having a top portion 14, a bottom portion 16 and a central portion 18, a bladder 20 positioned between the bottom portion 16 and the central portion 18 of the applicator body 12 and designed for holding alcohol solution, a hinge lever 22 extending from an inner side of the central portion and extending outwards from the top portion of the applicator body and a hinge door 24 positioned on the central portion 18 of the applicator body 12. The improved applicator 10 allows easy application of alcohol solution to the patient's skin in a simple and safe manner.

Figure 2:
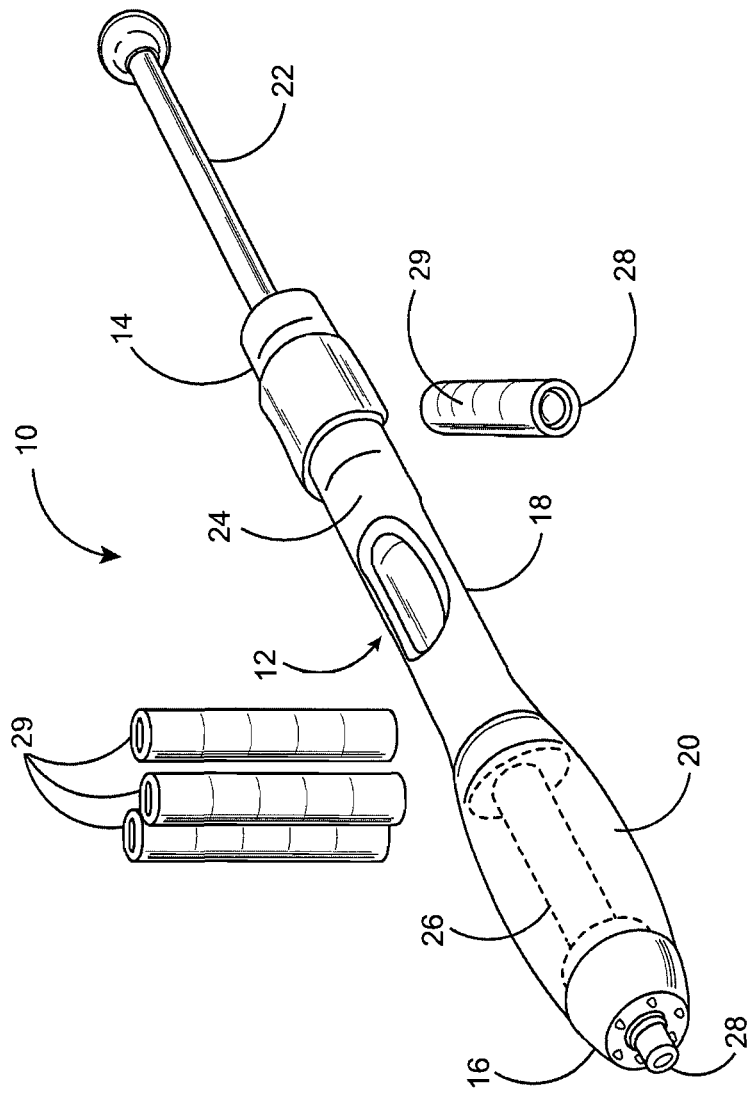
FIG. 2 illustrates a perspective view of the improved applicator of the present invention, four cartridges of swabs, each cartridge comprised of approximately five swabs.

FIG. 2 illustrates a perspective view of the improved applicator 10 of the present invention, showing at least one cartridge 29 of swabs 26. The hinge door 24 is provided to load at least one cartridge 29 of swabs 26 in the central portion 18 of the applicator body 12. The new swabs can be easily loaded by opening the hinge door 24 and pulling back the hinge lever 22. The hinge lever 22 is spring-loaded which allows for the pulling back of the hinge lever 22 for loading and holding at least one or multiple cartridges 29 of swabs 26 in place within the applicator body 12. The cartridge 29 of swabs 26 rests between the bottom portion 16 and the central portion 18 of the applicator body 12. A top portion of at least one swab 28 extends outwards from the bottom portion 16 of the applicator body 12. The applicator body 12 is a hollow plastic tubing in such a way that the hinge lever 22 can easily pass through the central portion 18.

Figure 3:
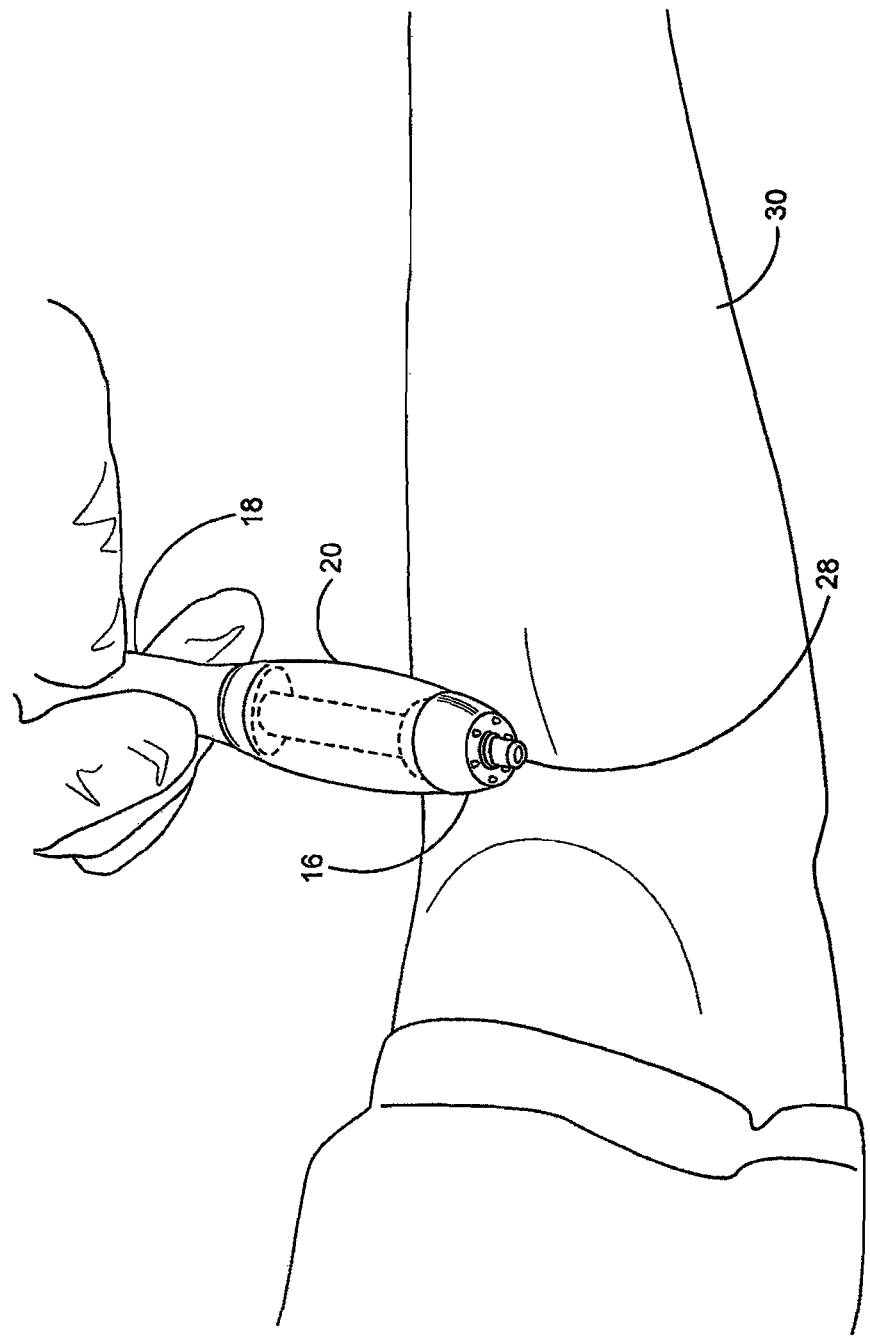
FIG. 3 illustrates a perspective view of the improved applicator of the present invention in use.
Figure 4:
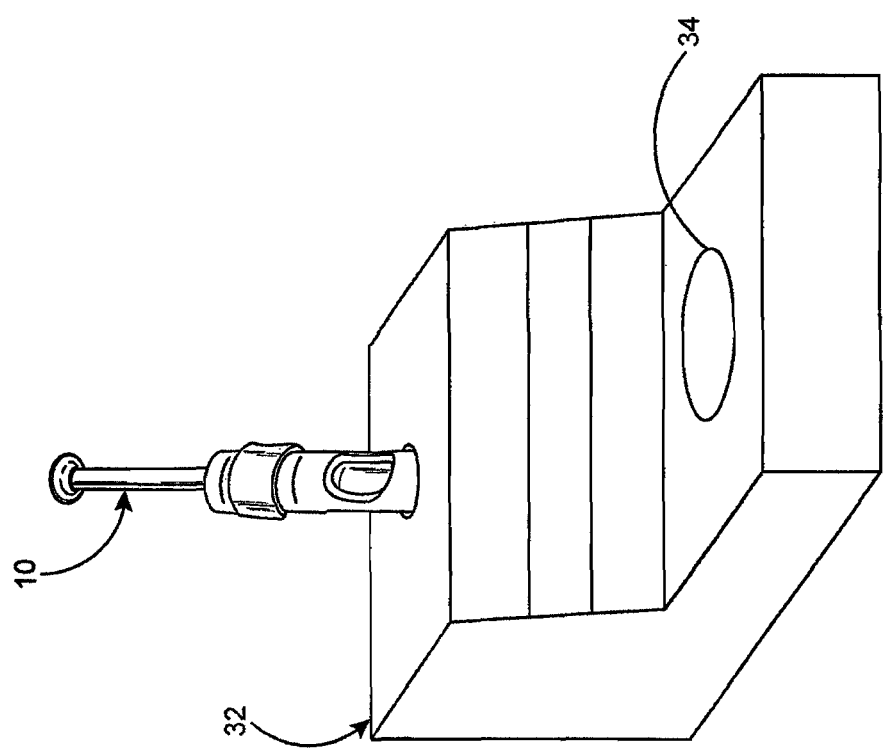
FIG. 4 illustrates a perspective view of the improved applicator of the present invention placed in an alcohol applicator.

Turning to FIG. 3, a perspective view of the improved applicator 10 of the present invention in use is illustrated. The top portion of the at least one swab 28 can be utilized to apply the alcohol solution on the patient's skin 30. The used swabs can be easily discarded by clicking the hinge lever 22 once. The clicking of the hinge lever 22 is accomplished by pressing the hinge lever 22 into the applicator body 12. The hinge lever is spring-loaded, so when released it returns to the original position. Thus, the improved applicator 10 provides a safe and convenient hand-held method for safe preparation of skin. Utilizing the improved applicator 10, the flow of alcohol solution can also be adjusted. The improved applicator 10 also provides more hygiene and safety to the patient. The improved applicator 10 is made of plastic and is easy to use. FIG. 4 illustrates a perspective view of the improved applicator 10 of the present invention placed in an applicator holder 32. The improved applicator 10 can be placed in the applicator holder 32 while not in use. The applicator holder 32 includes a fill port 34 that holds the alcohol solution. The improved applicator 10 can be easily refilled with alcohol by squeezing the bladder 20 and placing the bladder 20 in the alcohol solution contained in the fill port 34. The bladder 20 can be then taken out from the fill port 34 and the improved applicator can be again placed in the applicator holder 32.

FIG. 4 illustrates a perspective view of the improved applicator 10 of the present invention placed in an applicator holder 32. The improved applicator 10 can be placed in the applicator holder 32 while not in use. The applicator holder 32 includes a fill port 34 that holds the alcohol solution. The improved applicator 10 can be easily refilled with alcohol by squeezing the bladder 20 and placing the bladder 20 in the alcohol solution contained in the fill port 34 so as to allow the bladder 20 to expand by taking in the alcohol solution. The squeezing of the bladder 20 controls or adjusts the flow of solution by controlling whether the bladder 20 is partially or completely filled with solution, controlling the amount of solution taken into or released from the bladder 20. The bladder 20 can be then taken out from the fill port 34 and the improved applicator can be again placed in the applicator holder 32.

Figure 5:
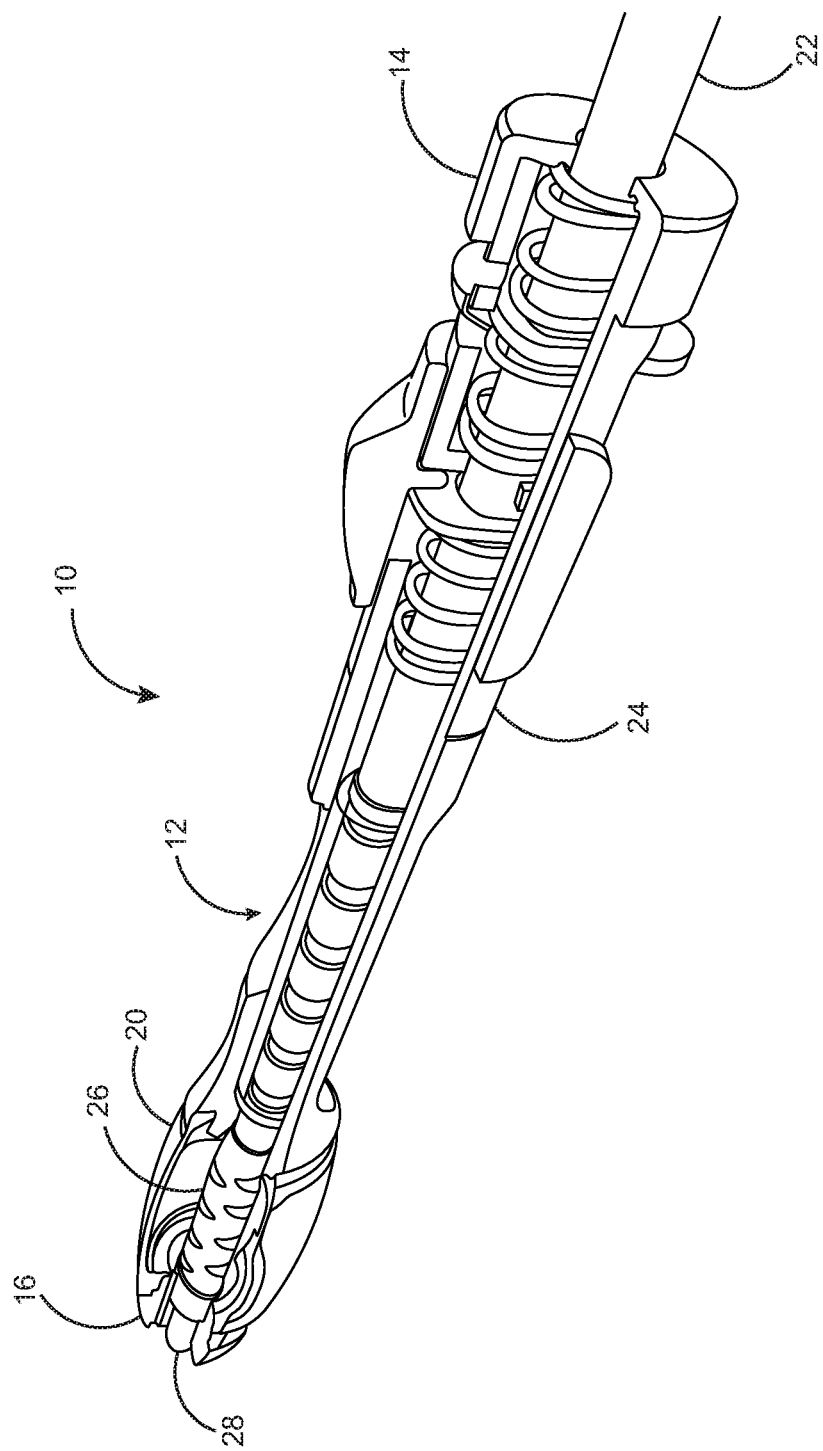
FIG. 5 illustrates an internal view of the improved applicator of the present invention, with a full view of the spring-loaded hinge lever or spring plunger.

FIG. 5 illustrates an internal view of the improved applicator 10 of the present invention, showing the spring-loaded hinge lever 22, and multiple cartridges of swabs 26 installed within the applicator body 12.

Figure 6:
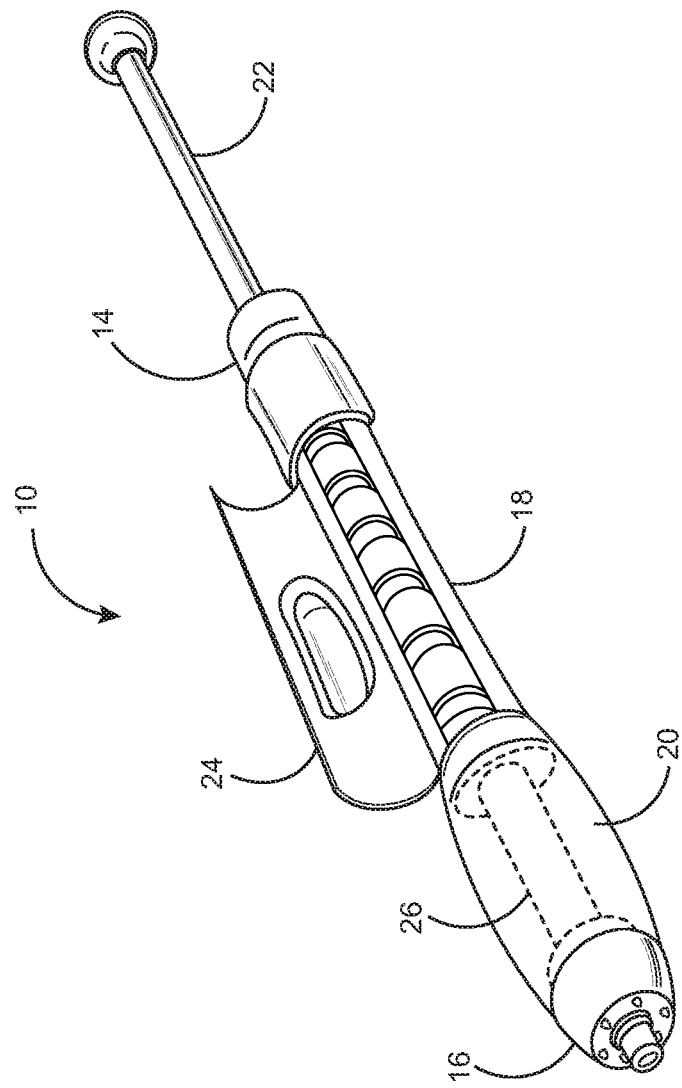
FIG. 6 illustrates a perspective view of the improved applicator of the present invention, showing the hinge door in an open position.

FIG. 6 shows the hinge door 24 of the improved applicator 10 in an open position, and multiple cartridges of swabs 26 installed within the applicator body 12.

What is claimed is:

1. An improved applicator for application of an alcohol solution prior to medical procedures comprising:
   an applicator body comprising a top portion connected to a central portion, the central portion connected to a squeezable bladder, and the squeezable bladder connected to a bottom portion, the central portion and the squeezable bladder each defining a separate hollow internal chamber;
   the hollow internal chamber of the central portion integral to the applicator body is designed to hold at least one cartridge having a plurality of swabs, each swab having a top portion for application of an alcohol solution;
   the hollow internal chamber of the squeezable bladder integral to the applicator body is designed for holding alcohol solution and for holding at least one of the plurality of swabs, and the bladder capable of being squeezed to allow for an alcohol solution to fill an interior of the bladder and to release the solution from the bladder;
   a spring-loaded hinge lever extending from the internal chamber of the central portion of the applicator body and extending outwards from the top portion of the applicator body for loading and ejecting individual swabs from the cartridge;
   a hinge door positioned on the central portion of the applicator body, the hinge door being provided to load and remove the cartridge of swabs in the internal chamber of the central portion;

wherein the spring-loaded hinge lever is used to advance at least one swab from the cartridge held in the central portion through the bladder and then through an opening of the bottom portion of the applicator body for the application of alcohol solution to a patient's skin, such that only the top portion of the swab touches a patient's skin, causing the applicator to have minimal contact with a patient's skin;

wherein the internal chamber of the squeezable bladder can be partially or wholly filled with alcohol solution by squeezing the bladder, the squeezing of the bladder allowing a user to adjust the flow of alcohol solution on the patient's skin;

wherein the bladder is squeezed to release alcohol solution through the bottom portion of the applicator body, which is absorbed by the at least one swab protruding from the opening of the bottom portion of the applicator body; and whereby the improved applicator allows for the application of an alcohol solution to a patient's skin with minimal contact, and allows the user to control and adjust the flow of alcohol solution to be applied to a patient's skin.

2. The improved applicator of claim 1 wherein the cartridge of swabs can be easily loaded into and removed from the central portion of the applicator body by opening the hinge door and pulling back the hinge lever.

3. The improved applicator of claim 1 wherein the hinge lever is pressed causing one individual swab to be released from the at least one cartridge of swabs and then move and rest between the bottom portion and the bladder of the applicator body.

4. The improved applicator of claim 1 wherein a top portion of at least one swab extends outwards from the bottom portion of the applicator body.

5. The improved applicator of claim 4 wherein the top portion of the at least one swab can be utilized to apply the alcohol solution on the patient's skin.

6. The improved applicator of claim 5 wherein the at least one swab is discarded by clicking the hinge lever once to eject the swab from the applicator body.

7. The improved applicator of claim 1 wherein the applicator can be refilled with alcohol solution by squeezing the bladder and placing the opening of the bottom portion of the applicator body in the alcohol solution to allow the solution to flow upwards into the bladder of the applicator body, then releasing the bladder when the bladder interior is partially or wholly filled with the solution.

8. The improved applicator of claim 1 wherein the improved applicator adjusts the flow of alcohol solution by squeezing the bladder of the applicator body to control the release of alcohol solution from the bladder.

9. The improved applicator of claim 1 wherein the improved applicator is placed in an application holder while not in use.

10. The improved applicator of claim 1 wherein the improved applicator is made of plastic.

11. The improved applicator of claim 6 wherein another swab is released from the cartridge and pushed through the bladder and the bottom portion of the applicator body in preparation for use by clicking the hinge lever.

12. The improved applicator of claim 1 wherein the applicator body is configured to hold multiple cartridges of swabs.

* * * * *